US011435370B2

(12) United States Patent
Yamada et al.

(10) Patent No.: US 11,435,370 B2
(45) Date of Patent: Sep. 6, 2022

(54) DATA ANALYING DEVICE AND PROGRAM FOR DATA ANALYSIS

(71) Applicant: Shimadzu Corporation, Kyoto (JP)

(72) Inventors: Yoshihiro Yamada, Kyoto (JP); Koretsugu Ogata, Kyoto (JP); Hiroto Tamura, Kani (JP); Teruyo Kato, Aisai (JP)

(73) Assignee: SHIMADZU CORPORATION, Kyoto (JP)

( * ) Notice: Subject to any disclaimer, the term of this patent is extended or adjusted under 35 U.S.C. 154(b) by 669 days.

(21) Appl. No.: 16/477,958

(22) PCT Filed: Nov. 9, 2017

(86) PCT No.: PCT/JP2017/040441
§ 371 (c)(1),
(2) Date: Jul. 15, 2019

(87) PCT Pub. No.: WO2018/131274
PCT Pub. Date: Jul. 19, 2018

(65) Prior Publication Data
US 2019/0369128 A1 Dec. 5, 2019

(30) Foreign Application Priority Data
Jan. 16, 2017 (JP) .............................. JP2017-004843

(51) Int. Cl.
*G01N 35/00* (2006.01)
*H01J 49/00* (2006.01)

(52) U.S. Cl.
CPC .... *G01N 35/00732* (2013.01); *H01J 49/0036* (2013.01); *G01N 2035/00831* (2013.01)

(58) Field of Classification Search
CPC .................. G01N 35/00732; H01J 49/0036
(Continued)

(56) References Cited

U.S. PATENT DOCUMENTS

2014/0288852 A1 9/2014 Ojima et al.
2015/0218640 A1* 8/2015 Brandon ................ G16B 25/20
506/7

(Continued)

FOREIGN PATENT DOCUMENTS

JP 2013-85517 A 5/2013
JP 2016-200435 A 12/2016

OTHER PUBLICATIONS

Tanaka et al., "Mass++: A Visualization and Analysis Tool for Mass Spectrometry", Journal of Proteome Research, Jul. 7, 2014, vol. 13, No. 8, doi:10.1021/pr500155z, ISSN 1535-3893, pp. 3846-3853 (total 8 pages).

(Continued)

*Primary Examiner* — Allyson N Trail
(74) *Attorney, Agent, or Firm* — Sughrue Mion, PLLC (57) ABSTRACT

A sample group forming section 24 classifies samples derived from microorganisms into groups according to empirical information showing the species or strain of each sample. A differential analysis section 27 performs a differential analysis using a peak matrix created based on the result of the grouping. An operator enters group rearrangement conditions concerning the drug resistance of microorganisms. Under the entered conditions, a sample group rearranging/rearrangement-cancelling section 25 rearranges the already formed groups by selecting or merging groups using another kind of previously registered empirical information which shows the drug resistance of each group. The differential analysis section 27 performs a differential analysis using a peak matrix newly created based on the result of the rearrangement of the groups. Thus, differential analysis results concerning the resistance to different drugs can be sequentially acquired as the group rearrangement condition is successively changed.

6 Claims, 5 Drawing Sheets

(58) Field of Classification Search
USPC .......................................................... 702/19
See application file for complete search history.

(56) References Cited

U.S. PATENT DOCUMENTS

| | | | |
|---|---|---|---|
| 2019/0113520 A1* | 4/2019 | Blume | G16H 50/30 |
| 2020/0370122 A1* | 11/2020 | Zhou | G01N 33/57415 |
| 2021/0113605 A1* | 4/2021 | Anderson | A61K 47/6803 |
| 2021/0278391 A1* | 9/2021 | Wang | A61K 31/381 |

OTHER PUBLICATIONS

Anonymous, "Mass++ Beginners' Guide", Mass++ Beginners' Guide, May 15, 2014, URL: https://www.shimadzu.co.jp/aboutus/ms_r/n00kbc0000006dat-att/MassBeginners_en.pdf, (Oct. 15, 2018), pages I-IV,1-112 (total 116 pages).

Communication dated Apr. 29, 2020 from European Patent Office in EP Application No. 17891371.1.

International Search Report with a Translation of Written Opinion in International Application No. PCT/JP2017/040441, dated Feb. 13, 2018.

Yudai Hotta, et al., "Classification of the Genus *Bacillus* Based on MALDI-TOF MS Analysis of Ribosomal Proteins Coded in S10 and spc Operons", Journal of Agricultural and Food Chemistry, 2011, vol. 59, No. 10, p. 5222-5230 (5 pages total).

\* cited by examiner

Fig. 3A
CONCEPT OF PEAK MATRIX

Fig. 3B
EXAMPLE OF PEAK MATRIX

| m/z | Group01 | | | | | Group02 | | | |
|---|---|---|---|---|---|---|---|---|---|
| | Sample 01-1 | Sample 01-2 | Sample 01-3 | Sample 01-4 | Sample 02-1 | Sample 02-2 | Sample 02-3 | Sample 02-4 | |
| 200.21 | 3.51E+05 | 3.54E+05 | 3.22E+04 | 2.76E+04 | 1.84E+04 | 1.85E+04 | 4.69E+04 | 3.36E+04 | |
| 2010.4 | 4.12E+04 | 6.44E+04 | 3.55E+04 | 1.36E+05 | 1.03E+04 | 1.13E+04 | 3.93E+04 | 1.60E+04 | |
| 2023.49 | 2.55E+05 | 2.52E+05 | 2.54E+04 | 0 | 7.45E+05 | 0 | 4.26E+05 | 7.63E+05 | |
| 2043.74 | 5.99E+04 | 7.41E+04 | 4.23E+04 | 1.93E+04 | 4.50E+04 | 6.98E+04 | 3.03E+04 | 3.57E+04 | |
| 2070.17 | 1.42E+04 | 5.44E+04 | 1.74E+04 | 3.66E+03 | 1.90E+05 | 3.58E+05 | 1.56E+05 | 3.47E+05 | |
| ... | | | | | | | | | |

Fig. 4

Fig. 5A
BEFORE GROUP REARRANGEMENT

Fig. 5B
AFTER GROUP REARRANGEMENT

Fig. 6

Fig. 7A
EXAMPLE OF DRUG RESISTANCE OF GROUPS

|     | D01 | D02 | D03 | D04 | D05 |
|-----|-----|-----|-----|-----|-----|
| G01 | +   | +   | +   | +   | −   |
| G02 | +   | +   | +   | +   | +   |
| G03 | −   | −   | −   | +   | −   |
| G04 | −   | −   | −   | −   | −   |

Fig. 7B
EXAMPLE OF GROUP REARRANGEMENT CONDITIONS

| | D01 | D02 | D03 | D04 | D05 | | AFTER REARRANGEMENT |
|---|---|---|---|---|---|---|---|
| RG(1) | + | | | | | ⇒ | G01 + G02 |
| RG(2) | − | | | | | ⇒ | G03 + G04 |
| RG(3) | | | + | + | | ⇒ | G01 + G02 + G03 |

DATA ANALYING DEVICE AND PROGRAM FOR DATA ANALYSIS

CROSS REFERENCE TO RELATED APPLICATIONS

This application is a National Stage of International Application No. PCT/JP2017/040441 filed Nov. 9, 2017, claiming priority based on Japanese Patent Application No. 2017-004843 filed Jan. 16, 2017.

TECHNICAL FIELD

The present invention relates to a data analyzing device for analytically processing data acquired by an instrumental analysis on a sample, and a computer program for such a device. More specifically, the present invention relates to a data analyzing device and a program for data analysis configured to perform a differential analysis between a plurality of sample groups.

BACKGROUND ART

In recent years, research on an analysis of biomarkers using mass spectrometry has been promoted for early diagnosis of specific diseases or confirmation of therapeutic effects. A portion of those techniques have already been put into practical use. For example, if a substance is discovered which does not exist or barely exists in blood, urine or other types of biological samples collected from healthy individuals, but definitely exists in blood, urine or other types of biological samples collected from patients suffering from certain diseases such as cancer, the substance can be considered to be a promising candidate of the biomarker for the disease in question. A typical approach to searching for such a biomarker is to perform a measurement using a mass spectrometer on a considerable number of samples derived from each of the two or more groups (e.g. a group of healthy individuals and a group of patients), and to perform a differential analysis between the groups based on the data obtained by the measurement.

A conventional and typical procedure for a differential analysis of mass spectrometric data aimed at searching for a biomarker (or any type of generally known marker) is as follows. It is hereinafter assumed that the total number of groups is $N_G$, and that of the samples is $N_S$.

[Step A1] A mass spectrum is acquired for each of a considerable number of samples ($N_S$), and a peak detection is performed in each mass spectrum according to a predetermined algorithm. Then, a peak list which shows the mass-to-charge ratio (m/z) values and signal intensities of the detected peaks, is created for each mass spectrum. The total number of peak lists to be created is the same as that of the samples, $N_S$.

[Step A2] The given samples can be classified into $N_G$ groups based on empirical information (prior information). Accordingly, the peak lists obtained in Step A1 are divided into $N_G$ groups, and a "peak matrix" $M_P$ is created in which each peak list is regarded as a column vector, with the signal-intensity values arranged in rows and columns so that signal-intensity values corresponding to the same mass-to-charge ratio are located in the same row. A peak detected in one mass spectrum may not have its counterpart located at the same mass-to-charge ratio in another mass spectrum (i.e. no counterpart in the peak list). In that case, a value of zero can be used as the signal-intensity value of the peak in question in the latter mass spectrum. An example of the empirical information is a piece of information which shows the origin of the sample, such as a piece of information showing whether the sample was collected from a healthy individual or a cancer patient.

Figure 3A:
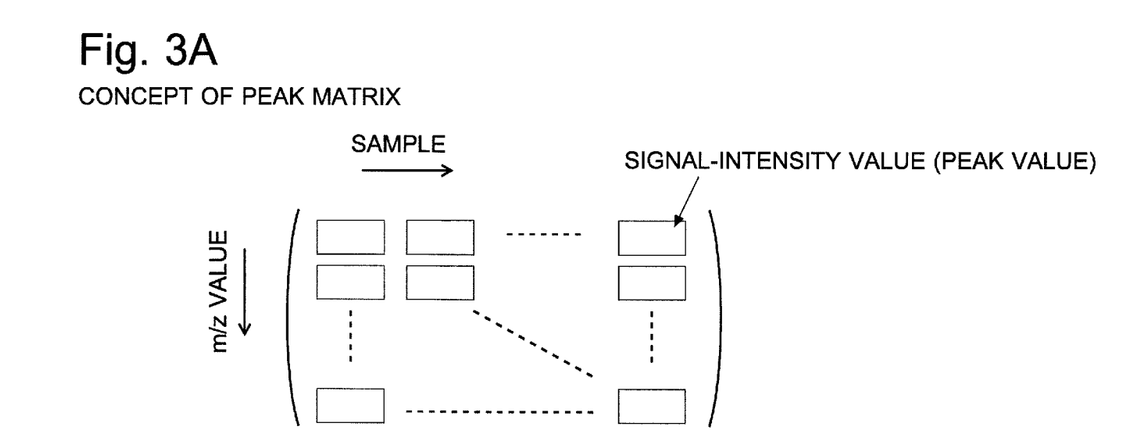
FIG. 3A is a conceptual diagram of a peak matrix.

FIG. 3A is a conceptual diagram of the peak matrix. In this peak matrix, the sample information (e.g. sample numbers) is arranged in the horizontal direction (in a row), while the mass-to-charge-ratio values are arranged in the vertical direction (in a column). Each element of the matrix is a signal-intensity value. The total number of columns of this peak matrix $M_P$ is equal to the number of samples $N_S$. The total number of rows is equal to the number of all peaks $N_P$ detected across the entire group of samples (without allowing the peaks detected at the same mass-to-charge-ratio value to be counted multiple times).

[Step A3] For each row of the peak matrix $M_P$ created in Step A2, a univariate analysis (which is typically a t-test, U-test, analysis of variance (ANOVA) or similar statistical hypothesis testing) is performed to determine whether or not there is a significant difference between the groups. Then, the p-value, which shows the statistical reliability of the observed difference, is calculated for each row.

[Step A4] The p-value of each row is compared with a predetermined significance level $\alpha$ (for example, $\alpha=0.05$ is often used in the t-test) to extract a row, i.e. a peak (or mass-to-charge ratio), at which there is a significant difference between the groups. A substance corresponding to this extracted peak is a marker candidate.

The grouping of the samples into the group of healthy individuals and the group of patients in the previously described example is unambiguous. However, it is often the case that the samples to be analyzed in an actual differential analysis cannot be grouped in a single definite manner. There is also a strong demand for the differential analysis to be performed on the same set of samples using various grouping methods based on different kinds of empirical information, to search for a marker for each grouping method.

For example, in recent years, mass spectrometric techniques for distinguishing or identifying the species or strains of microorganisms have been drawing attention (see Patent Literature or Non-Patent Literature 1). A mass spectrometric process for identifying a microorganism normally includes the steps of assigning a plurality of samples of the same species or strain to one group and performing a differential analysis to search for a mass spectrum peak showing a significant difference between different groups, i.e. between different species or strains. Meanwhile, different species or strains of microorganisms may have some properties or features in common. For example, it is often the case for different species or strains of microorganisms to have common features, such as a specific drug (antibiotic) being particularly effective for different species or strains of microorganisms, or conversely, the different species or strains of microorganisms being resistant to a specific drug. In such cases, it may be necessary to conduct research for each drug to search for a marker which yields a significant difference between a group of samples resistant to one or more drugs and a group of samples having no such resistance, in addition to the search for a marker which yields a significant difference between different species or strains of microorganisms.

In the previously described type of differential analysis, every time the criterion for the grouping (i.e. the kind of empirical information to be used for the grouping) is changed, an operator (user) needs to perform an input operation for each individual sample to specify the group which the sample should belong to according to the new criterion. If there is a considerable number of samples, such a task will be extremely cumbersome and lower the efficiency of the analysis. The same task also constitutes a cause of an inappropriate analysis due to input errors.

CITATION LIST

Patent Literature

Patent Literature 1: JP 2013-85517 A

Non-patent Literature

Non-Patent Literature 1: Y. Hotta and four other authors, "Classification of the Genus *Bacillus* Based on MALDI-TOF MS Analysis of Ribosomal Proteins Coded in S10 and spc Operons", *Journal of Agricultural and Food Chemistry*, 2011, Vol. 59, No. 10, pp. 5222-5230

SUMMARY OF INVENTION

Technical Problem

The present invention has been developed to solve the previously described problem. Its objective is to provide a data analyzing device and a program for data analysis to be used for a differential analysis based on data acquired for each sample in order to locate a marker for distinguishing between a plurality of groups of samples, where the device or program allows an operator to appropriately change the criterion for the grouping based on the properties, features or other factors which the operator is focused on, and to easily and efficiently perform a differential analysis between the new groups according to the criterion after the change.

Solution to Problem

The data analyzing device according to the present invention developed for solving the previously described problem includes:
a) a data acquiring section configured to acquire data for each of a plurality of samples, the data representing a chromatogram or mass spectrum;
b) an empirical information setting section configured to acquire or set one or more kinds of empirical information for each of the plurality of samples, the empirical information showing a property of each sample;
c) an empirical information selecting section configured to allow an operator to select a condition for grouping based on the one or more kinds of empirical information;
d) a group forming section configured to perform grouping of the plurality of samples into a plurality of groups based on the selected condition for grouping; and
e) a differential analysis section configured to analyze a difference in a peak of the chromatogram or mass spectrum between the plurality of groups formed by the group forming section, using the data acquired by the data acquiring section and grouped into the plurality of groups,
where the data analyzing device is configured to execute the grouping in the group forming section and a differential analysis in the differential analysis section according to a selecting operation by the operator using the condition selecting section.

The program for data analysis according to the present invention developed for solving the previously described problem is a program for data analysis configured to run on a computer to process data for a plurality of samples so as to perform a differential analysis between a plurality of groups into which the plurality of samples are to be classified, based on data representing a chromatogram or mass spectrum acquired for each of the plurality of samples, where the program is configured to make the computer execute a differential analysis including:
a) an empirical information setting step configured to acquire or set one or more kinds of empirical information for each of the plurality of samples, the empirical information showing a property of each sample;
b) a condition selecting step configured to allow an operator to select a condition for grouping based on the one or more kinds of empirical information;
c) a group forming step configured to perform grouping of the plurality of samples into the plurality of groups based on the selected condition for grouping; and
d) a differential analysis step configured to analyze a difference in a peak of the chromatogram or mass spectrum between the plurality of groups formed in the group forming step, using the data grouped into the plurality of groups,
where the computer executes the grouping in the group forming step and a differential analysis in the differential analysis step according to a selecting operation by the operator in the condition selecting step.

In the data analyzing device and the program for data analysis according to the present invention, the data to be analyzed is mass spectrum data collected by a mass spectrometric analysis (including $MS^n$ spectrum data where n is an integer equal to or greater than two), or chromatogram data collected by a gas chromatographic or liquid chromatographic analysis.

In the data analyzing device according to the present invention, the data acquiring section acquires chromatogram data or mass spectrum data for each of a plurality of samples by reading the data, for example, from an external storage device. The empirical information setting section acquires, for each of the samples, one or more kinds of empirical information showing a property of the sample by automatically reading the information from an external source, or sets the empirical information according to a manual input by an operator or similar users. The empirical information may include an item of information showing the history or origin of each sample. The condition selecting section allows the operator to select the condition for grouping based on one kind of empirical information which the operator is focused on among the one or more kinds of empirical information which are previously set in the previously described manner. As a specific example, the condition selecting section may display choices of the grouping condition based on one kind of empirical information, or information equivalent to such choices, on a screen of a display unit so that the operator can select and indicate one of the choices with an input unit.

After the grouping condition has been selected by the operator through the condition selecting section, the group forming section responds to the selecting operation and perform the grouping of the plurality of samples to be analyzed into a plurality of groups based on the selected grouping condition. The differential analysis section performs a differential analysis for locating a difference in a peak of the chromatogram or mass spectrum between the groups, using the data corresponding the samples included in each of the plurality of groups formed in the previously described manner. The result of the differential analysis is shown on the screen of the display unit. There is no specific limitation on the method for the differential analysis; for example, statistical hypothesis testing may preferably be used, such as the analysis of variance (ANOVA). A peak which yields a significant difference between the groups can be extracted from the data by the differential analysis. The mass-to-charge ratio, retention time, or substance corresponding to that peak can be used as a marker for distinguishing between the groups.

In a preferable mode of the data analyzing device according to the present invention, the group forming section is configured to perform grouping of the plurality of samples into N groups based on first empirical information concerning each sample, where N is an integer equal to or greater than three, and the data analyzing device further includes:

f) a group rearrangement condition specifying section configured to allow an operator to specify a condition for rearranging the groups using second empirical information concerning each of the N groups formed by the group forming section, or concerning the samples included in each of the N groups; and g) a group rearranging section configured to form M groups, where N>M, by selecting one or more groups from the N groups formed by the group forming section and merging the selected groups together as needed, based on the condition for rearranging the groups specified through the group rearrangement condition specifying section, where the differential analysis section is configured to perform a differential analysis between the N groups formed by the group forming section, using the data corresponding to the samples included in each of the N groups, and to perform a differential analysis between the M groups formed by the group rearranging section, using the data corresponding to the samples included in each of the M groups.

According to this mode of configuration, the group forming section perform the grouping of the plurality of samples to be analyzed into N groups based on the first empirical information given to each sample, where N is equal to or greater than three. Normally, the first empirical information is a piece of information for classifying a considerable number of samples into a minimum size of groups.

Typically, the first empirical information is a piece of information showing the history, origin or other aspects of each sample. This information can be included in the sample name or sample identification number given to each sample. This allows the operator to locate the first empirical information in the sample name, sample identification number or similar information of each sample, and manually indicate the group to which the sample should be assigned. In this case, the group forming section can perform the grouping of the samples into N groups according to the indication. Automatic sorting of the samples based on the sample name, sample identification number or similar information is also possible if the first empirical information is included in the sample name, sample identification number or similar information of each sample. In this case, the group forming section can locate the sample name, sample identification number or similar information, and automatically perform the grouping of the samples into N groups based on the located information. The result of the grouping, i.e. the information concerning the samples assigned to each group, may preferably be shown on the screen of the display unit so that the operator can check the result.

Consider the situation in which the operator is going to perform a differential analysis between new groups after merging two or more groups which are similar to each other in a specific property into one group among the groups formed by the group forming section. The operator specifies the group rearrangement condition through the group rearrangement condition specifying section so that the groups labeled with the second empirical information indicating the possession of that specific property should be selected. Based on the specified group rearrangement condition, the group rearranging section rearranges the groups, for example, by selecting two or more groups having that specific property using the second empirical information given to the N groups, and then merging the selected groups into one group as well as merging the other groups into another group. The operator can change the group rearrangement condition specified through the group rearrangement condition specifying section. In that case, the group rearranging section changes the combination of the groups to be selected and merged together. As with the result of the grouping, the result of the group rearrangement, i.e. the information concerning the samples assigned to each group after the rearrangement, may preferably be shown on the screen of the display unit.

In this configuration, the differential analysis section additionally performs the differential analysis between the M rearranged groups formed in the previously described manner, using the data corresponding to the samples included in each of these groups. This differential analysis is based on the M groups which have been formed according to a criterion that is different from the one applied to the differential analysis based on the N groups mentioned earlier. By this analysis, a new peak which yields a significant difference between the groups under the new criterion, i.e. a new marker, can be extracted from the data. Every time the operator changes the group rearrangement condition specified through the group rearrangement condition specifying section in the previously described manner, the differential analysis section performs a new differential analysis based on the rearranged groups. Accordingly, the operator can consecutively specify different properties and search for a marker related to each property.

In the data analyzing device according to the present invention, the group-rearrangement condition specifying section may preferably be configured to allow the operator to cancel the group rearrangement condition by a command which restores the grouping to the original state and allows the operator to newly specify a different group rearrangement condition.

In the data analyzing device according to the present invention, if the data is mass spectrum data, the data analyzing device may further include:

h) a peak detecting section configured to detect peaks from mass spectrum data and create a peak list which shows a signal-intensity value for each of the mass-to-charge ratios of the detected peaks; and i) a peak matrix creating section configured to create a peak matrix based on the peak lists created for the plurality of samples as well as based on the result of the grouping by the group forming section or the result of the group rearrangement by the group rearranging section, the peak matrix having signal-intensity values as elements arranged in rows and columns in such a manner that the mass-to-charge-ratio values of the peaks are assigned in a row while information which identifies the samples sorted into groups is assigned in a column, and the differential analysis section is configured to perform a differential analysis on the peak matrix.

The rows and columns in the aforementioned peak matrix are defined for convenience; it is evident that the rows and columns can be transposed. In other words, it is evident that replacing the terms "row" and "column" with each other does not substantially change the previously described configuration.

In the previously described configuration, the peak matrix creating section receives mass spectrum data corresponding to each sample and detects peaks in each mass spectrum according to a predetermined criterion. There is no specific limitation on the predetermined criterion; any commonly known peak-detection method may be used. For example, among the peak-shaped signals observed on a mass spectrum, each signal whose intensity is equal to or higher than a predetermined value may be detected as a true peak, whereas each signal whose intensity is lower than the predetermined value may be considered to be a noise peak. After the peaks have been detected in all mass spectra, the signal-intensity value and mass-to-charge-ratio value of each peak are acquired, and a peak matrix having the signal-intensity values as its elements is created, in which the mass-to-charge-ratio value is assigned in a row, while the information identifying the sample is assigned in a column. The samples assigned in a column should be sorted by the group based on the result of the grouping or that of the group rearrangement. One row in the peak matrix is an array of signal-intensity values for all samples at one specific mass-to-charge ratio.

The differential analysis section performs a differential analysis on the peak matrix by an appropriate method, such as the analysis of variance. In this case, the differential analysis section can extract a peak or mass-to-charge ratio corresponding to a row or column which shows a significant difference in the differential analysis. The substance corresponding to this peak or mass-to-charge ratio serves as a marker for distinguishing between groups.

There is no limitation on the kind of sample to be analyzed in the data analyzing device according to the present invention. As a preferable mode of the present invention, the sample to be analyzed is a microorganism, and the first empirical information is information showing the species and/or strain of the microorganism.

In this case, the second empirical information may be information showing the presence or absence of the resistance to various drugs (antibiotics or antimicrobial agents), or information showing minimum inhibitory concentrations (MIC) or clinically determined thresholds of the drugs.

According to this mode of the invention, it is possible to detect a substance which serves as a marker for distinguishing between species or strains of microorganisms. It is also possible to detect a substance which serves as, or seems to be useful as a marker for distinguishing a microorganism that is characteristically resistant to one specific kind of drug or resistant to a plurality of specific kinds of drugs (i.e. multiple-drug resistant).

Advantageous Effects of Invention

The data analyzing device and the program for data analysis according to the present invention allow an operator to appropriately change the criterion for the grouping based on a property or feature which the operator is focused on, and to easily and efficiently perform a differential analysis between the new groups according to the criterion after the change. Thus, the operator can efficiently detect a substance which serves as a marker that is significantly related to the property or feature of interest.

DESCRIPTION OF EMBODIMENTS

An embodiment of the mass spectrometry system employing a data analyzing device according to the present invention is hereinafter described with reference to the attached drawings.

Figure 1:
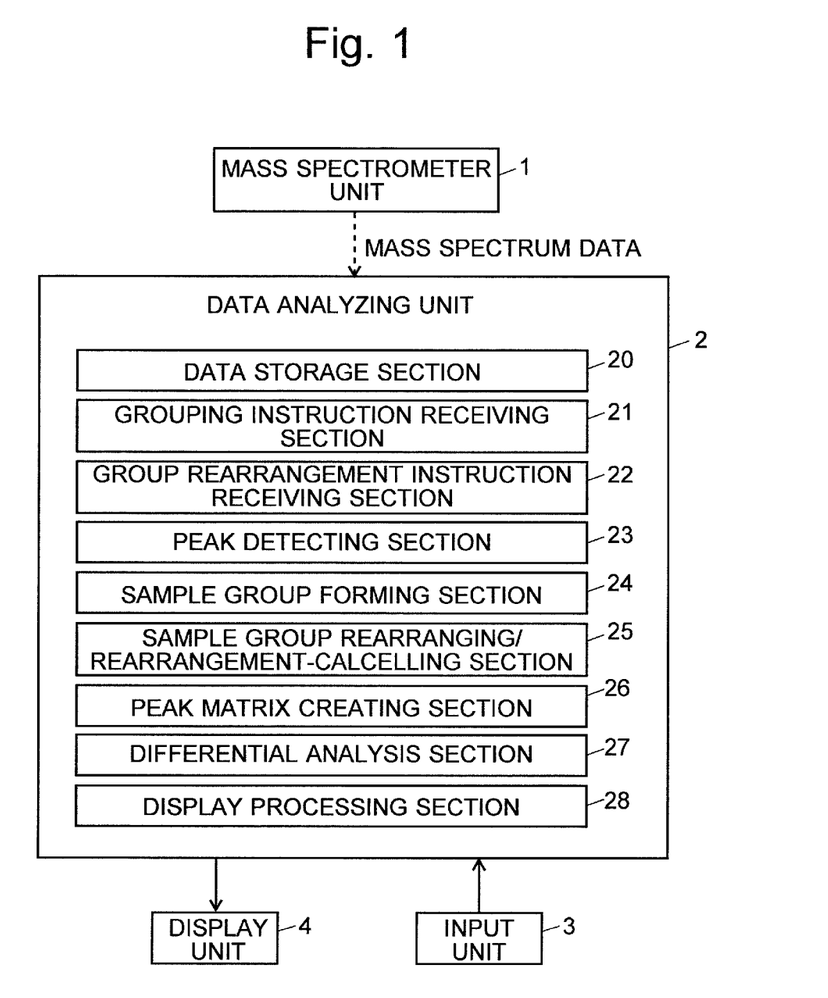
FIG. 1 is a schematic configuration diagram of one embodiment of a mass spectrometry system employing a data analyzing device according to the present invention.

FIG. 1 is a schematic configuration diagram of the mass spectrometry system according to the present embodiment.

The mass spectrometry system according to the present embodiment includes: a mass spectrometer unit 1 which performs mass spectrometric analyses on samples to acquire mass spectrum data, i.e. signal intensity data over a specific range of mass-to-charge ratios m/z; a data analyzing unit 2 which carries out a differential analysis by analytically processing mass spectrum data collected with the mass spectrometer unit 1; an input unit 3 for allowing an operator (user) to input information or issue commands; and a display unit 4 for showing windows for the operator to enter information or issue commands, and for displaying the results of analyses.

The mass spectrometer unit 1 may be any type and have any configuration. For example, a matrix assisted laser desorption ionization time-of-flight mass spectrometer, which can collect mass spectrum data with a high level of mass resolving power and high level of detection sensitivity, may be used.

The data analyzing unit 2 includes a data storage section 20, grouping instruction receiving section 21, group rearrangement instruction receiving section 22, peak detecting section 23, sample group forming section 24, sample group rearranging/rearrangement-cancelling section 25, peak matrix creating section 26, differential analysis section 27, and display processing section 28 as its functional blocks in order to execute characteristic data-analyzing processing, which will be described later.

The actual form of the data analyzing unit 2 is normally a personal computer or more sophisticated type of computer. The aforementioned functional blocks can be realized by executing, on such a computer, dedicated data-processing software installed on the same computer. In that case, the input unit 3 includes a keyboard and pointing device (e.g. mouse) of the computer, while the display unit 4 is a monitor. In such a configuration, a portion or the entirety of the data-processing software installed on the computer corresponds to the program for data analysis according to the present invention.

Figure 2:
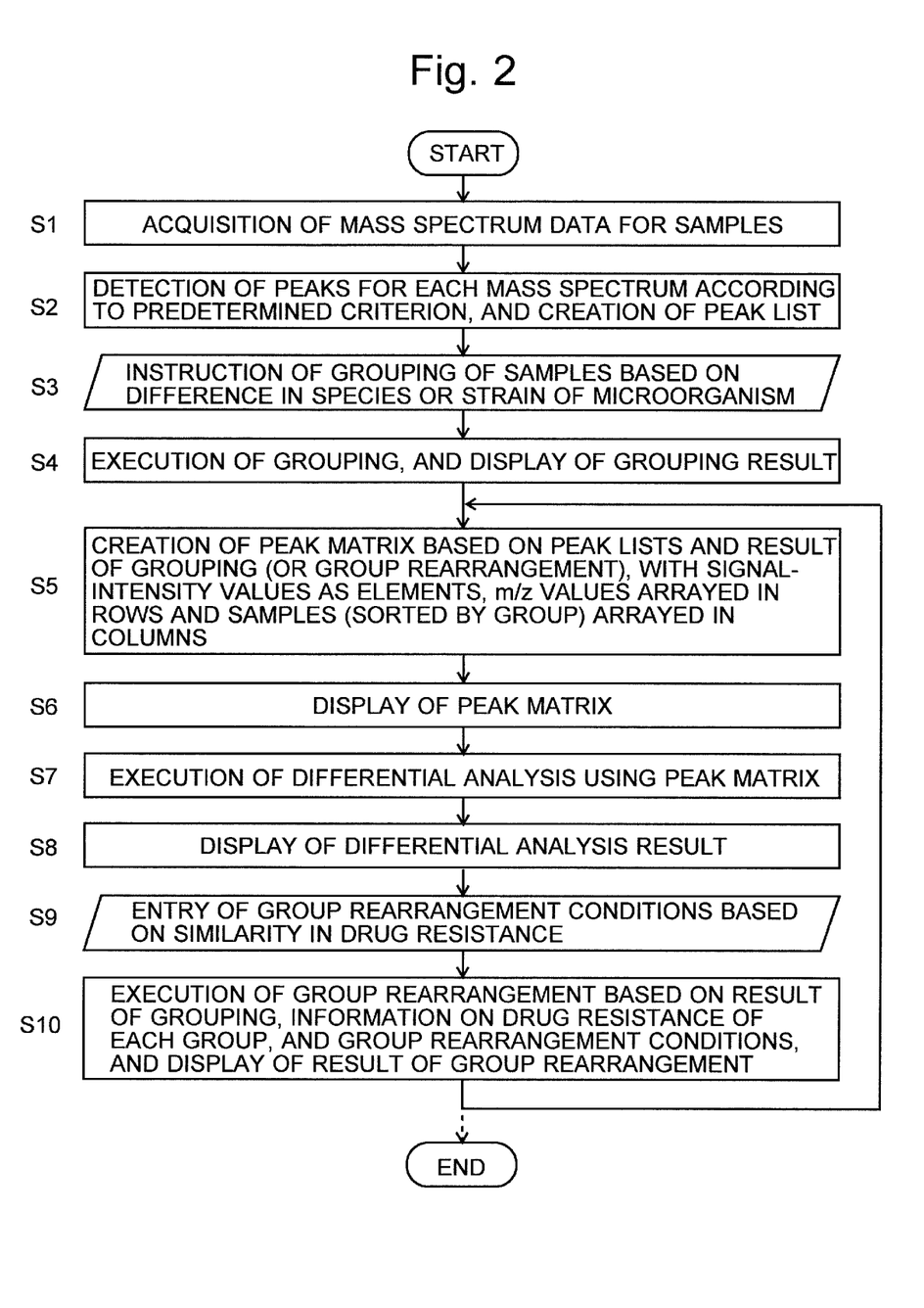
FIG. 2 is a flowchart showing the process steps of a differential analysis in the mass spectrometry system according to the present embodiment.

The following descriptions deal with the tasks to be performed by an operator and the processing to be performed by the data analyzing unit 2 in the mass spectrometry system according to the present embodiment with reference to FIG. 2, taking an example in which a differential analysis is used to search for a marker for distinguishing between microorganisms (e.g. bacteria or viruses) in terms of their resistance to specific drugs (e.g. antibiotics or antimicrobe agents).

In the mass spectrometry system according to the present embodiment, mass spectrum data acquired within a predetermined range of mass-to-charge ratios by a mass spectrometric analysis performed on given samples in the mass spectrometer unit 1 are continuously sent to the data analyzing unit 2. In the data analyzing unit 2, the mass spectrum data is labeled with sample identification information, such as the sample name, and stored as a separate data file for each sample in the data storage section 20. It should be noted that the data storage section 20 can be used to store not only mass spectra acquired with a specific mass spectrometer unit 1 shown in FIG. 1 but also mass spectrum data acquired in a similar manner in any other mass spectrometer. In other words, the mass spectrum data corresponding to a considerable number of samples to be analyzed in the data analyzing unit 2 may be a collection of data acquired with a single mass spectrometer or those acquired with a plurality of different mass spectrometers.

Every sample has a sample name which is previously given (normally, in advance of the mass spectrometric analysis). The sample name includes information showing the kind of species or strain of a microorganism. Specifically, the sample name has a specific form, such as "Sample 01-1", "Sample 01-2", . . . , in which the two-digit figure appended to "Sample" shows the classification of the species or strain. For example, "Sample 01-1" and "Sample 01-2" are two different samples of the same species (or strain), whereas "Sample 01-1" and "Sample 02-1" are different samples of different species (or strains). In the present example, the kind of species or strain corresponds to the first empirical information, or the entire sample name can be considered as the first empirical information. The sample name of each sample may be individually stored in the data file corresponding to that sample, or collectively stored in a separate file related to the data file.

It is hereinafter assumed that mass spectrum data acquired for a considerable number of samples, each of which is a microorganism, are each stored as a single data file along with the sample name in the data storage section 20.

The operator specifies a batch of data to be processed from the input unit 3 and issues a command to execute the processing. Upon receiving this command, the peak detecting section 23 sequentially reads and acquires the specified data files from the data storage section 20 (Step S1). Both the mass spectrum data of each sample and the empirical information of the sample are thereby obtained. The peak detecting section 23 processes each set of mass spectrum data to detect each peak on the mass spectrum according to a predetermined criterion and to determine the position (the value of mass-to-charge ratio m/z) and signal-intensity value of each detected peak. As for the peak detection algorithm, a commonly and conventionally known technique can be used. For example, a peak-like waveform having a signal intensity which exceeds a predetermined threshold can be detected as a peak. Then, the combinations of the mass-to-charge-ratio value and signal-intensity value of the detected peaks (there are normally multiple peaks) are gathered together and compiled into a peak list for each mass spectrum, i.e. for each sample (Step S2).

Subsequently, the operator views a window displayed on the display unit 4 by the grouping instruction receiving section 21 and operates the input unit 3 to give an instruction to classify the samples into different groups of species or strains according to the sample name which is one item of empirical information (Step S3). The sample group forming section 24 perform the grouping of the samples into groups according to the instruction and determines the set of samples to be assigned to each group. The display processing section 28 displays the result of the grouping on the screen of the display unit 4 (Step S4).

Figure 4:
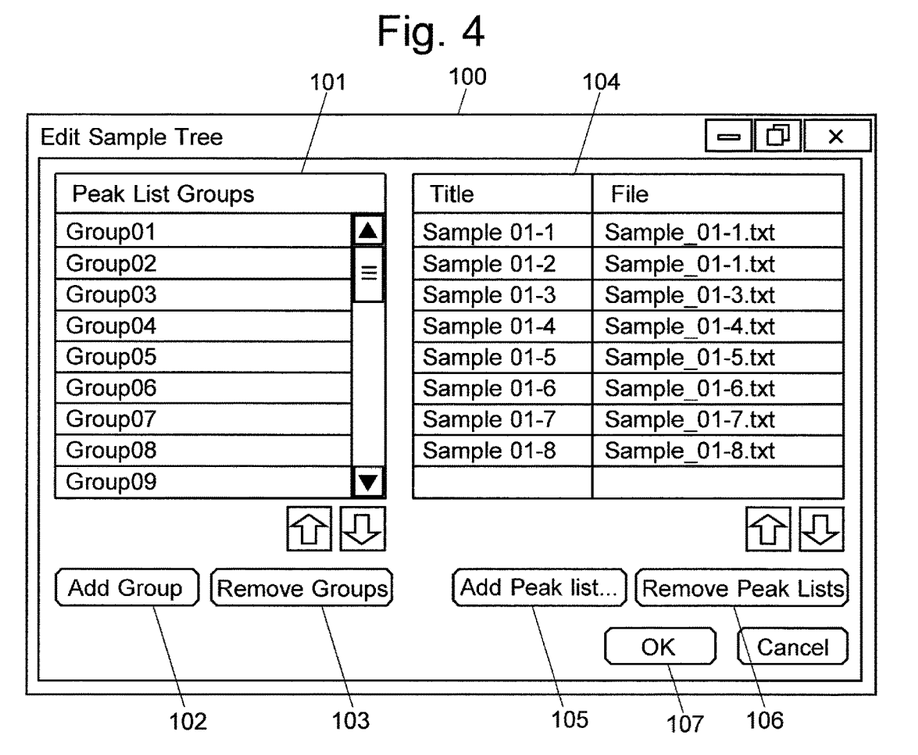
FIG. 4 is a diagram showing a grouping specification setting window in the mass spectrometry system according to the present embodiment.

A specific procedure for giving the grouping instruction and executing the grouping based on the instruction is as follows:

The operator performs a predetermined operation with the input unit 3, whereupon the grouping instruction receiving section 21 displays a grouping specification setting window 100 as shown in FIG. 4 on the screen of the display unit 4. The grouping specification setting window 100 includes a grouping list 101 and a sample list 104. The grouping list 101 is a list of groups. The sample list 104 is a list of sample names and data-file names to be assigned to a group selected in the group list 101. In the present example, the group names "Group01", "Group02", . . . are given to the groups to identify each group. The operator can increase the number of groups in the group list 101 by clicking the "Add Group" button 102 or decrease the number of groups (i.e. remove a group) by clicking the "Remove Groups" button 103. Similarly, the operator can add a sample to the selected group by clicking the "Add Peak List" button 105, or remove a sample from the group by clicking the "Remove Peak Lists" button 106.

In the present example, as noted earlier, the two-digit number included in the sample name is the first empirical information representing the species or strain of a microorganism. With the help of this number in the sample name, i.e. the first empirical information, the operator defines groups and sets samples which belong to each group so that samples of the same species or strain will be assigned to one group. In the example shown in FIG. 4, eight samples which are respectively named "Sample 01-1", "Sample 01-2", . . . and "Sample 01-8" contain a microorganism of the same species or strain, so that these samples are assigned to one group named "Group01". The operator enters and sets the samples to be assigned to each group in a manner as illustrated in FIG. 4. After this entering task has been completed for all groups, the operator clicks the "OK" button 107 to fix the instructions on the grouping and assignment of the samples. The sample group forming section 24 relates the fixed group names to the sample names of the samples according to the grouping instruction. Thus, the grouping of the samples is achieved.

Figure 5A:
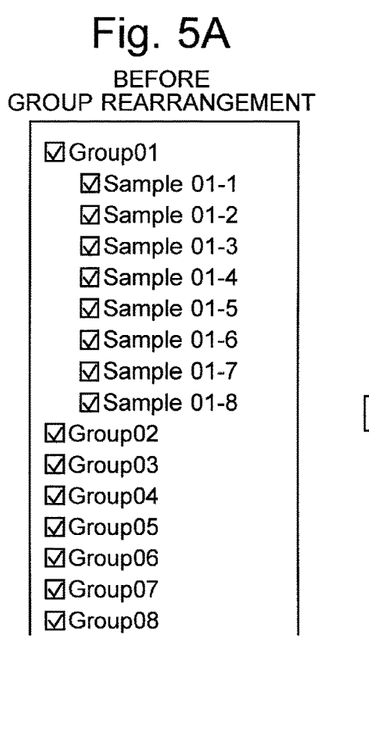
FIGS. 5A and 5B are diagrams showing a grouping result display window in the mass spectrometry system according to the present embodiment.

The operator subsequently performs a predetermined operation with the input unit 3, whereupon the display processing section 28 shows the information concerning the samples included in each group (in the present case, sample names) on the screen of the display unit 4, as shown in FIG. 5A. This allows the operator to visually check the appropriateness of the assignment of the samples to the groups. If the sample assignment is incorrect, or if the assignment needs to be changed, the operator can return to Step S3 and correct the sample assignment.

Understandably, it is not always necessary to perform the setting so that all samples for which the peak lists have been created are exhaustively classified into the groups; samples which should be excluded from the analysis do not need to be assigned to any group. Accordingly, for example, even if data files corresponding to samples named "Sample 06-1", "Sample 06-2", . . . are present in the data storage section 20, a group named "Group06" which only contains this species or strain of samples will not be necessarily created. As another example, even if a data file corresponding to a sample named "Sample 06-1" is present in the data storage section 20, and there is a group named "Group06" to which samples named "Sample 06-2", . . . have been assigned, it does not necessarily mean that "Sample 06-1" must also be included in "Group06".

The previous description assumes that the task of adding or removing a group is performed by the operator. It is also possible to automatically perform the grouping task according to a predetermined condition using, for example, the sample name, identification number or other similar kinds of information given to each sample. In the previous example, the two-digit figure appended to "Sample" in the sample name stands for the species or strain of a microorganism. This figure can be automatically located and used to sort samples into a plurality of groups. It is naturally possible to allow the operator to manually delete unnecessary groups or remove unnecessary samples from the groups after the automatic grouping has been performed.

Subsequently, the peak matrix creating section 26 arranges all or some of the peak lists created in Step S2 according to the grouping result obtained in Step S4, and creates a peak matrix (Step S5).

Specifically, as shown in FIG. 3A, the peak matrix is created by arranging the signal-intensity values as its elements in such a manner that the mass-to-charge-ratio values of the peaks in the peak list corresponding to each sample are arranged in the vertical direction (in a column), while the samples are arranged in the horizontal direction (in a row). The samples assigned in a row should be sorted by the group. Accordingly, if the grouping is changed in a manner to be described later, the order of the samples assigned in a row in the peak matrix should also be changed. There may be a mass-to-charge-ratio value at which a peak is present in one sample, but its counterpart is not present in another sample. In a row which corresponds to such a mass-to-charge-ratio value, the element corresponding to the "counterpart" is actually missing. Accordingly, a signal-intensity value of zero can be given to such an element.

Figure 3B:
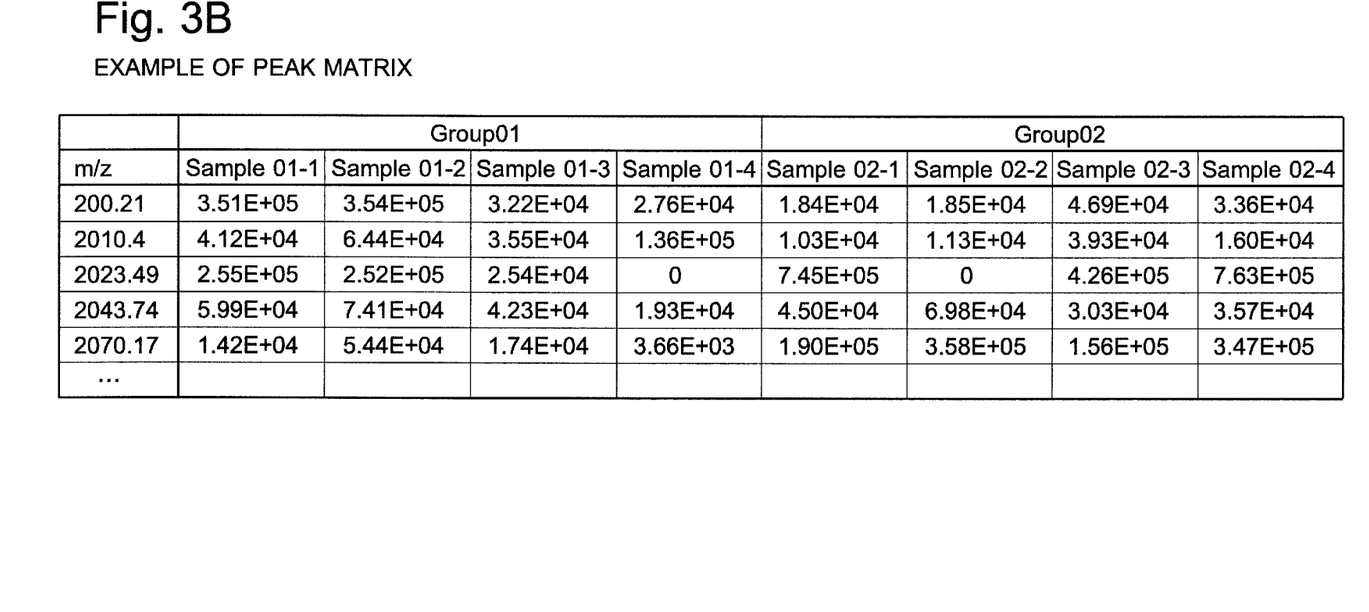
FIG. 3B is one example of the peak matrix.

The display processing section 28 shows the created peak matrix on the screen of the display unit 4 to present it to the operator (Step S6). FIG. 3B shows one example of the peak matrix created in such a manner.

The differential analysis section 27 receives the created peak matrix and performs a differential analysis using the peak matrix according to a predetermined algorithm (Step S7). There is no specific limitation on the technique of the differential analysis. If there are three or more groups, ANOVA can be used as statistical hypothesis testing, since ANOVA is suited for the multi-group testing. ANOVA can yield p-values, as with the t-test or similar other techniques. Based on the p-value calculated for each row in such a differential analysis, it is possible to determine whether or not the row shows a significant difference between the groups.

The display processing section 28 shows the result of the differential analysis on the screen of the display unit 4 (Step S8). In the displayed result of the differential analysis, a row of the matrix (i.e. a peak) which yields a significant difference between the groups can be highlighted so as to present, to the operator, the mass-to-charge ratio of that peak as a marker candidate. In the initial grouping based on the first empirical information, since each group includes samples derived from the same species or strain of microorganism, a marker which is useful for distinguishing between different species or strains of microorganisms is obtained as the result of the differential analysis.

Microorganisms derived from different species or strains, i.e. samples belonging to different groups formed by the previously described grouping process, may be resistant to the same drug or the same set of drugs. Therefore, in the study of multiple-drug resistance or similar area, it is important to locate a marker which can be used to distinguish between a group of microorganisms which are resistant to one or more drugs and a group of the other microorganisms (which have no such resistance) across multiple species or strains. When a search for such a marker needs to be performed, a continued analysis should be performed as follows.

In order to perform the new grouping related to the drug resistance mentioned earlier, the second empirical information which is different from the first empirical information is used. The second empirical information shows, for each species or strain of microorganism, what kinds of drugs the microorganism is resistant to. It is hereinafter assumed that a piece of information which describes whether or not a group is resistant to each of the drugs named "Drug01", "Drug02" is previously entered as the second empirical information for each group in the data analyzing unit 2 and stored in the data storage section 20. Such information may be manually entered by the operator with the input unit 3, or the system may read a data file describing such information and automatically store the information in the data storage section 20.

Figure 6:
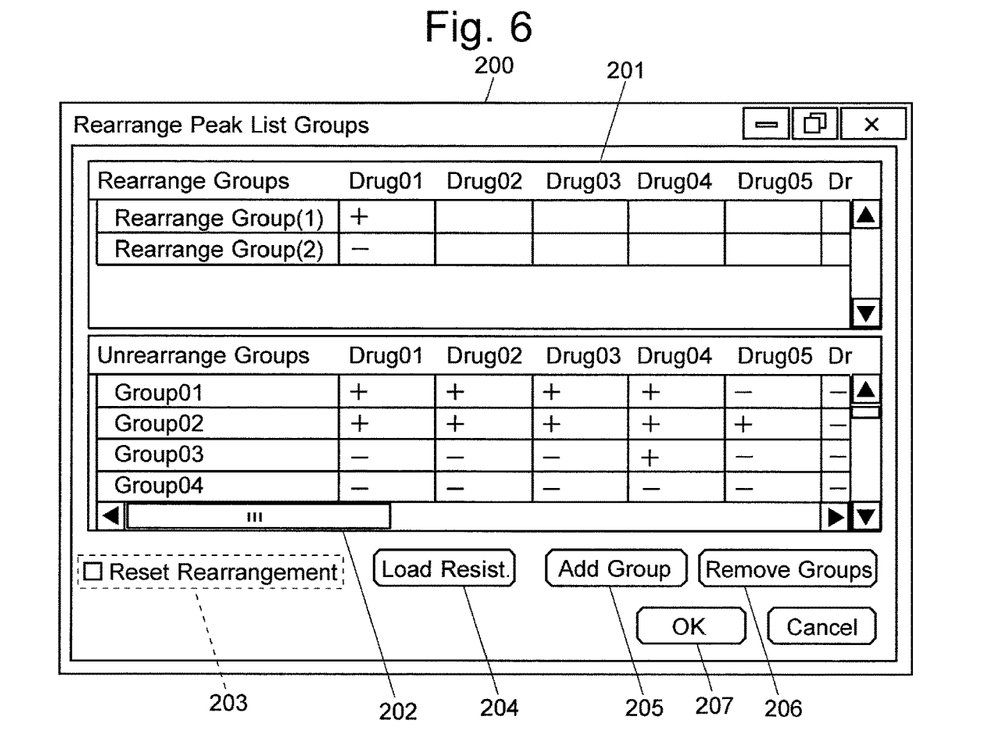
FIG. 6 is a diagram showing a group rearrangement specification setting window in the mass spectrometry system according to the present embodiment.

The operator performs a predetermined operation with the input unit 3 to initiate the grouping based on the drug resistance which is the second empirical information. Then, the group rearrangement instruction receiving section 22 displays a group rearrangement specification setting window 200 as shown in FIG. 6 on the screen of the display unit 4. The group rearrangement specification setting window 200 includes a rearranged group list 201 and a drug-resistance evaluation list 202. The rearranged group list 201 is a list which shows the groups after the rearrangement. The drug-resistance evaluation list 202 is a list which shows the groups before the rearrangement (these groups are hereinafter called the "un-rearranged groups") along with the information which shows whether or not a group is resistant to a drug for each combination of the group and drug. This drug-resistance evaluation list 202 is blank immediately after the group rearrangement specification setting window 200 is opened for the first time. The operator specifies a predetermined data file containing the second empirical information and clicks the "Load Resist." button 204, whereupon the group rearrangement instruction receiving section 22 reads the contents of the data file and displays the drug-resistance evaluation list 202 as shown in FIG. 6. In this list, the "plus (+)" and "minus (−)" signs assigned to each of the drugs named "Drug01", "Drug02", . . . indicate that the corresponding group is resistant ("+") or non-resistant ("−") to the drug. In the example of FIG. 6, "Group01" is resistant to the four drugs named "Drug01", "Drug02", "Drug03" and "Drug04", whereas the same group is non-resistant to the drug named "Drug05".

The operator views the drug-resistance evaluation list 202 in the group rearrangement specification setting window 200, adds or removes one or more groups to or from the rearranged groups as needed, and sets the presence or absence of the resistance to each drug as the group rearrangement condition for each of the rearranged groups (Step S9). The operator can add a group to the rearranged groups in the rearranged group list 201 by clicking the "Add Group" button 205 or remove a group from the rearranged groups by clicking the "Remove Groups" button 206. In FIG. 6, two rearranged groups named "Rearrange Group(1)" and "Rearrange Group(2)" are set. The group rearrangement conditions are set so that the rearranged group named "Rearrange Group(1)" should be resistant ("+") to the drug named "Drug01", while the rearranged group named "Rearrange Group(2)" should be non-resistant ("−") to "Drug01". The operator can set the group rearrangement conditions by clicking each relevant field in the rearranged group list 201.

After the group rearrangement conditions including the rearranged groups have been set in the previously described manner, the operator clicks the "OK button" 207 to fix the group rearrangement conditions. The operator can entirely cancel the fixed group rearrangement conditions by clicking the "OK" button 207 after checking the "Reset Rearrangement" checkbox 203. This operation entirely resets the group rearrangement conditions which have been set in the rearranged group list 201, and thereby allows the operator to once more set the group rearrangement conditions.

Figure 7A:
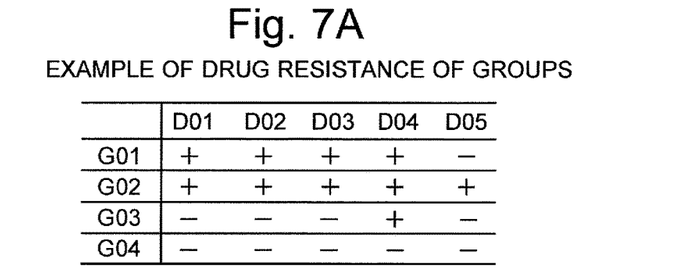
FIGS. 7A and 7B are diagrams showing an example of the rearrangement of the groups in the mass spectrometry system according to the present embodiment.
Figure 7B:
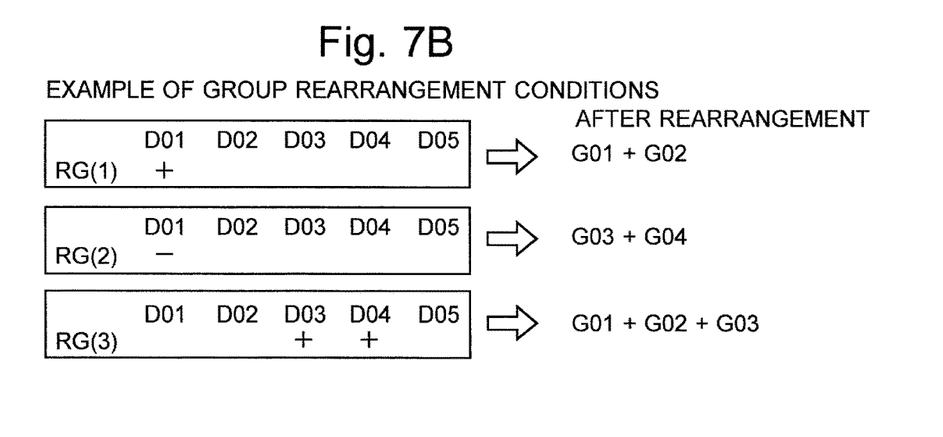

In response to the clicking of the "OK" button 207 after the group rearrangement conditions have been set, the sample group rearranging/rearrangement-cancelling section 25 selects groups according to the fixed group rearrangement conditions. If there are two or more un-rearranged groups corresponding to one rearranged group, those un-rearranged groups should be merged together. Thus, the rearranged groups and the samples included in each of these groups are fixed (Step S10). For example, consider the case of four un-rearranged groups having drug resistance as shown in FIG. 7A. Drug names are abbreviated as "D01", "D02", . . . in FIG. 7A. Suppose that there are three rearranged groups "RG(1)", "RG(2)" and "RG(3)" with their respective drug resistance set as shown in FIG. 7B. Under these conditions, groups "G1" and "G2" which are both resistant to drug "D01" are selected and merged together for rearranged group "RG(1)". Similarly, groups "G3" and "G4" which are both non-resistant to drug "D01" are selected and merged together for rearranged group "RG(2)". As for rearranged group "RG(3)", three groups "G1", "G2" and "G3" which are all resistant to at least one of the two drugs "D03" and "D04" are selected and merged together.

Figure 5B:
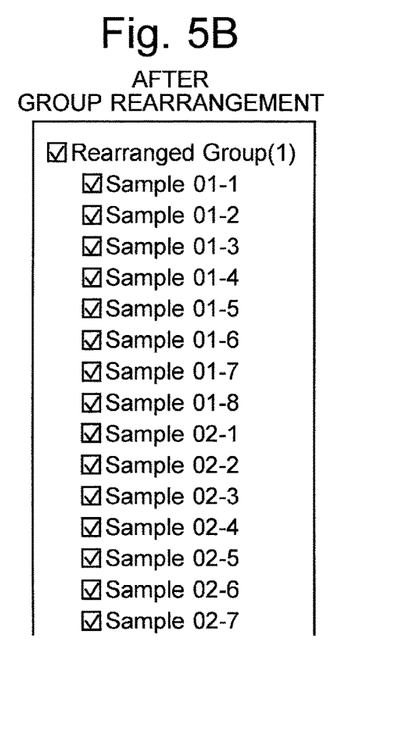

The operator subsequently performs a predetermined operation with the input unit 3, whereupon the display processing section 28 shows information (in the present example, sample names) concerning the samples included in the rearranged groups on the screen of the display unit 4, as shown in FIG. 5B. This allows the operator to visually check the appropriateness of the assignment of the samples to the rearranged groups.

Subsequently, the operation returns from Step S10 to Step S5. The peak matrix creating section 26 arranges all or some of the peak lists according to the result of the group rearrangement and once more creates a peak matrix. Then, the processes in Steps S6 through S8 are once more executed. That is to say, the differential analysis section 27 performs a differential analysis using the newly created peak matrix, and the result of the differential analysis is displayed on the screen of the display unit 4. As noted earlier, a change in the grouping leads to a change in the peak matrix. The change in the peak matrix naturally leads to a different result of the differential analysis.

By conducting the differential analysis while sequentially changing the group rearrangement condition in the previously described manner, the operator can obtain a differential analysis result corresponding to each of the group rearrangement conditions, i.e. the information concerning a marker for distinguishing between the groups formed under each of the group rearrangement conditions. Accordingly, by setting the group rearrangement condition which specifies the combination of the presence or absence of the resistance to one or more drugs that the operator is focused on, the operator can acquire detailed information concerning such drug resistance.

In the previously described example, the resistance to each drug is represented by a binary value of presence or absence. It is also possible to use a numerical value, such as the minimum inhibitory concentrations (MIC) of each drug or a clinically determined threshold, i.e. to use a multi-valued expression. This allows for more detailed setting of the group rearrangement conditions, such as a group whose MIC for a specific drug is equal to or higher than T.

The group rearrangement condition does not always need to be based on the drug resistance. It is possible to set group rearrangement conditions using various properties or features possessed by each species or strain of microorganism. Needless to say, different group rearrangement conditions require different kinds of empirical information.

It is evident that the samples to be analyzed with a data analyzing device according to the present invention is not limited to microorganisms. The present invention is applicable to various kinds of samples for which the differential analysis is useful. It is also evident that the present invention is available for not only the processing of mass spectrum data as in the previous embodiment; it can also be applied to chromatogram data obtained for samples with a gas chromatograph or liquid chromatograph.

Furthermore, it should be understood that any change, modification or addition appropriately made within the spirit of the present invention, other than those already described, will also naturally fall within the scope of claims of the present application.

REFERENCE SIGNS LIST

1 . . . Mass Spectrometer Unit
2 . . . Data Analyzing Unit
20 . . . Data Storage Section
21 . . . Grouping Instruction Receiving Section
22 . . . Group Rearrangement Instruction Receiving Section
23 . . . Peak Detecting Section
24 . . . Sample Group Forming Section
25 . . . Sample Group Rearranging/Rearrangement-Cancelling Section
26 . . . Peak Matrix Creating Section
27 . . . Differential Analysis Section
28 . . . Display Processing Section
3 . . . Input Unit
4 . . . Display Unit
100 . . . Grouping Specification Setting Window
101 . . . Group List
102, 205 . . . "Add Group" Button
103, 206 . . . "Remove Groups" Button
104 . . . Sample List
105 . . . "Add Peak List" Button
106 . . . "Remove Peak Lists" Button
107, 207 . . . "OK" Button
200 . . . Group Rearrangement Specification Setting Window
201 . . . Rearranged Group List
202 . . . Drug-Resistance Evaluation List
203 . . . "Reset Rearrangement" Checkbox
204 . . . "Load Resist." Button

The invention claimed is:

1. A data analyzing device, comprising:
   a data acquiring section configured to acquire data for each of a plurality of samples, the data representing a chromatogram or mass spectrum;
   an empirical information setting section configured to acquire or set a plurality of kinds of empirical information for each of the plurality of samples, the empirical information showing a property of each sample;
   a condition selecting section configured to allow an operator to select a condition for grouping based on first empirical information which is one of the plurality of kinds of empirical information;
   a group forming section configured to perform grouping of the plurality of samples into N groups based on the condition for grouping selected through the condition selecting section, where N is an integer equal to or greater than three;
   a group rearrangement condition specifying section configured to allow an operator to specify, for each of the N groups formed by the group forming section or for each of the samples included in each of the N groups, a condition for rearranging the N groups using second empirical information which is one of the plurality of kinds of empirical information;
   a group rearranging section configured to form M groups, where N>M, by selecting one or more groups from the N groups formed by the group forming section and merging the selected groups together as needed, based on the condition for rearranging the groups specified through the group rearrangement condition specifying section; and
   a differential analysis section configured to analyze a difference in a peak of the chromatogram or mass spectrum between a plurality of groups formed by the group forming section or the group rearranging section, using the data acquired by the data acquiring section and included in each of the groups,
   where the differential analysis section is configured to perform a differential analysis between the N groups formed by the group forming section, using the data corresponding to samples included in each of the N groups, and to perform a differential analysis between the M groups formed by the group rearranging section, using the data corresponding to samples included in each of the M groups.

2. The data analyzing device according to claim 1, wherein:
   the data is a mass spectrum data, and the data analyzing device further comprises:
   a peak detecting section configured to detect peaks from mass spectrum data and create a peak list which shows a signal-intensity value for each of the mass-to-charge ratios of the detected peaks; and
   a peak matrix creating section configured to create a peak matrix based on the peak lists created for the plurality of samples as well as based on a result of the grouping by the group forming section or a result of group rearrangement by the group rearranging section, the peak matrix having signal-intensity values as elements arranged in rows and columns in such a manner that the mass-to-charge-ratio values of the peaks are assigned in a row while information which identifies the samples sorted into groups is assigned in a column, and
   the differential analysis section is configured to perform a differential analysis on the peak matrix.

3. The data analyzing device according to claim 2, wherein:
   the differential analysis section is configured to extract a peak or mass-to-charge ratio corresponding to a row or column which shows a significant difference in the differential analysis.

4. The data analyzing device according to claim 1, wherein:
   the sample to be analyzed is a microorganism, and the first empirical information is information showing the species and/or strain of the microorganism.

5. The data analyzing device according to claim 4, wherein:
   the second empirical information is information showing presence or absence of resistance to a drug, or information showing a minimum inhibitory concentration (MIC) or a clinically determined threshold of a drug.

6. A non-transitory computer readable medium recording a program for data analysis configured to run on a computer to process data for a plurality of samples so as to perform a differential analysis between a plurality of groups into which the plurality of samples are to be classified, based on data representing a chromatogram or mass spectrum acquired for each of the plurality of samples, wherein:
   the program is configured to make the computer operate to execute:
   an empirical information setting step configured to acquire or set a plurality of kinds of empirical information for each of the plurality of samples, the empirical information showing a property of each sample;
   a condition selecting step configured to allow an operator to select a condition for grouping based on first empirical information which is one of the plurality of kinds of empirical information;
   a group forming step configured to perform grouping of the plurality of samples into N groups based on the condition for grouping selected in the condition selecting step, where N is an integer equal to or greater than three;
   a first differential analysis step configured to analyze a difference in a peak of the chromatogram or mass spectrum between the N groups formed in the group forming step, using the data corresponding to samples grouped into the N groups;
   a group rearrangement condition specifying step configured to allow an operator to specify, for each of the N groups formed in the group forming step or for each of the samples included in each of the N groups a condition for rearranging the groups using second empirical information which is one of the plurality of empirical information;
   a group rearranging step configured to form M groups, where N>M, by selecting one or more groups from the N groups formed in the group forming step and merging the selected groups together as needed, based on the condition for rearranging the groups specified in the group rearrangement condition specifying step; and
   a second differential analysis step configured to analyze a difference in a peak of the chromatogram or mass spectrum between the M groups formed in the group rearranging step using the data corresponding to samples included in each of the M groups.

* * * * *